United States Patent
Butz et al.

(10) Patent No.: US 6,936,564 B2
(45) Date of Patent: Aug. 30, 2005

(54) SUPPORTED CATALYST CONSISTING OF METAL OF THE PLATINUM GROUP AND OBTAINED BY MEANS OF CONTROLLED ELECTROLESS DEPOSITION

(75) Inventors: Thomas Butz, Ludwigshafen (DE); Henrik Junicke, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 88 days.

(21) Appl. No.: 10/381,595

(22) PCT Filed: Oct. 1, 2001

(86) PCT No.: PCT/EP01/11346

§ 371 (c)(1),
(2), (4) Date: Apr. 2, 2003

(87) PCT Pub. No.: WO02/28528

PCT Pub. Date: Apr. 11, 2002

(65) Prior Publication Data

US 2004/0013601 A1 Jan. 22, 2004

(30) Foreign Application Priority Data

Oct. 2, 2000 (DE) .......................... 100 48 844

(51) Int. Cl.⁷ ............................... B01J 31/00
(52) U.S. Cl. .................... 502/150; 427/98; 427/437; 427/443.1; 427/250
(58) Field of Search ............... 502/150; 427/98, 427/437, 443.1, 250

(56) References Cited

U.S. PATENT DOCUMENTS

| | | | |
|---|---|---|---|
| 4,471,014 A | | 9/1984 | Den Hartog et al. |
| 4,731,229 A | | 3/1988 | Sperandio |
| 5,320,821 A | | 6/1994 | Nagashima et al. |
| 5,347,046 A | * | 9/1994 | White et al. ........... 560/245 |
| 5,739,075 A | * | 4/1998 | Matusz ................. 502/302 |
| 5,767,276 A | * | 6/1998 | Zhang .................. 546/2 |
| 5,792,721 A | * | 8/1998 | Grate et al. ........... 502/209 |
| 5,985,235 A | * | 11/1999 | Nystrom et al. ........ 423/588 |
| 6,063,944 A | * | 5/2000 | Di Renzo et al. ...... 549/531 |
| 6,126,914 A | * | 10/2000 | Ogasawara et al. ..... 423/588 |
| 6,146,700 A | * | 11/2000 | Yuan et al. ........... 427/304 |
| 6,168,775 B1 | | 1/2001 | Zhou et al. |
| 6,472,556 B2 | * | 10/2002 | Kitchen et al. ........ 560/241 |
| 6,500,968 B2 | * | 12/2002 | Zhou et al. ........... 549/531 |
| 6,534,661 B1 | * | 3/2003 | Zhou et al. ........... 549/531 |
| 6,603,038 B1 | * | 8/2003 | Hagemeyer et al. ..... 560/241.1 |
| 6,630,118 B2 | * | 10/2003 | Paparatto et al. ...... 423/584 |
| 6,676,919 B1 | * | 1/2004 | Fischer et al. ........ 423/584 |

FOREIGN PATENT DOCUMENTS

| | | |
|---|---|---|
| DE | 20 46 521 | 3/1972 |
| DE | 29 34 584 | 3/1981 |
| DE | 00/59635 | 10/2000 |
| EP | 0 448 884 | 10/1991 |
| EP | 0 754 664 | 1/1997 |
| EP | 0 878 235 | 11/1998 |

* cited by examiner

Primary Examiner—J. A. Lorengo
Assistant Examiner—Jennine Brown
(74) Attorney, Agent, or Firm—Oblon, Spivak, McClelland, Maier & Neustadt, P.C.

(57) ABSTRACT

The invention relates to a supported platinum group metal catalyst obtainable by controlled electroless deposition of at least one platinum group metal from a deposition solution which comprises
i) at least one homogeneously dissolved platinum group metal compound,
ii) a reducing agent and
iii) at least one control agent selected from isopolyacids and heteropolyacids of niobium, tantalum, molybdenum, tungsten and vanadium or their salts.

21 Claims, 1 Drawing Sheet

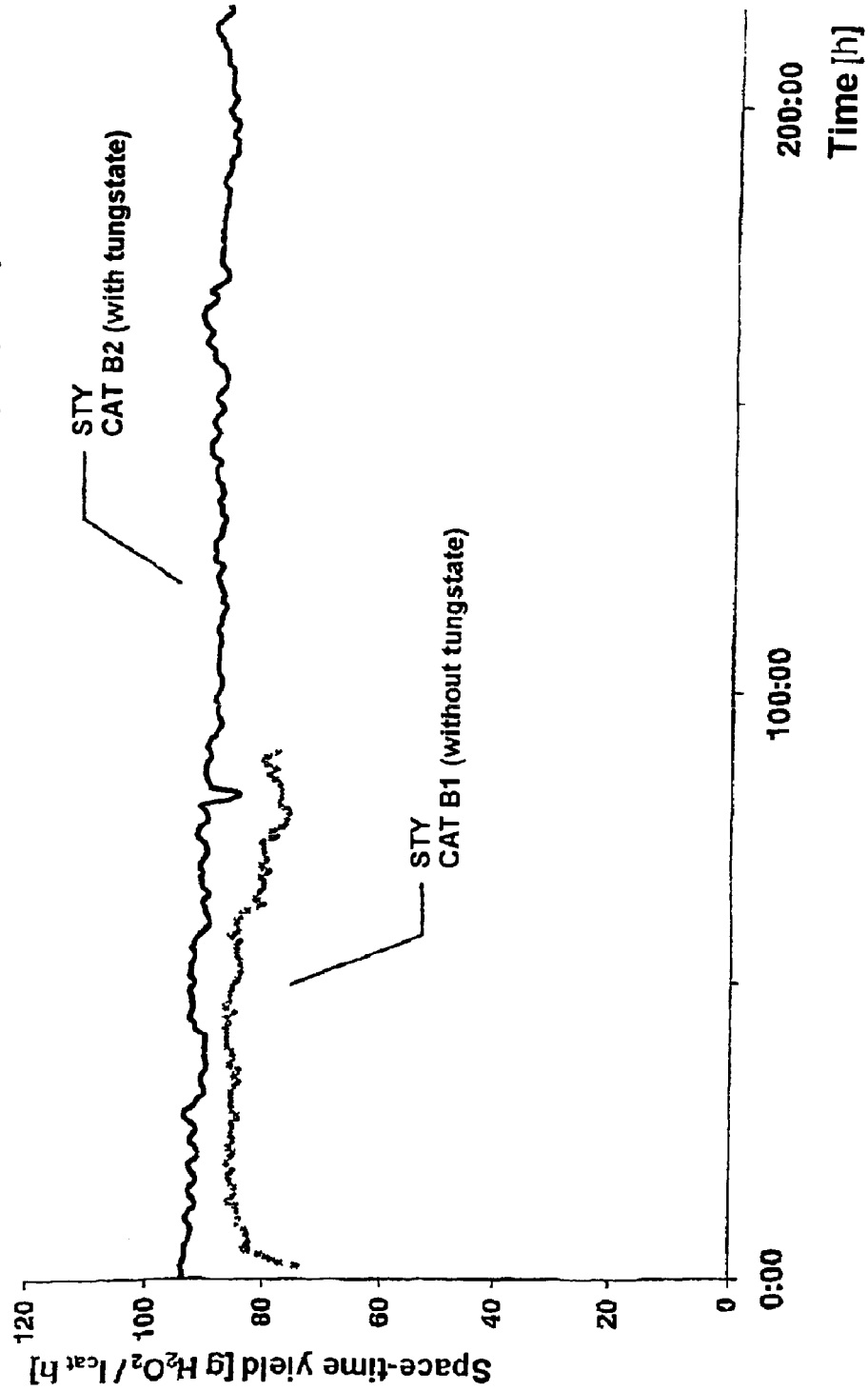
Figure 1: STY variation for catalyst according to the invention (= B2) and comparative catalyst (= B1)

SUPPORTED CATALYST CONSISTING OF METAL OF THE PLATINUM GROUP AND OBTAINED BY MEANS OF CONTROLLED ELECTROLESS DEPOSITION

The invention relates to a supported platinum group metal catalyst, to a process for preparing it by controlled electroless deposition and to a process for hydrogenating inorganic and organic compounds using the catalyst, in particular for direct synthesis of hydrogen peroxide.

Supported platinum group metal catalysts are used in numerous chemical processes, in particular for hydrogenating inorganic and organic compounds, and have attained great technical significance there. An intensively investigated reaction is what is known as the direct synthesis of hydrogen peroxide starting from molecular oxygen and hydrogen. There are endeavors to discover catalysts having a high activity and selectivity for this reaction and other hydrogenations.

U.S. Pat. No. 6,168,775 describes noble metal catalysts for the direct hydrogen peroxide synthesis. A noble metal salt solution is mixed with the solution of an ionic control polymer, for example a polyacrylate, having a molar mass between 300 and 8000 dalton and reduced with hydrogen before or after impregnating a support with the solution. The catalysts obtained in this way are said to be notable for a fine distribution of the noble metal on the support and for preferential formation of crystals having 110 and/or 220 crystal surfaces on the surface.

Many metals may be applied to supports by electroless deposition, also referred to as autocatalytic deposition. For example, EP-A-0 875 235 describes a process for preparing supported catalysts, in which a porous support is treated with a solution of a salt of the catalytically active metal and a reducing agent, and an electroless deposition of the catalytically active metal is achieved in this way.

WO 00/59635 describes a process for preparing platinum group metal catalysts on metallic supports, in which the metal is deposited in the form of discrete particles. The deposition is effected from an aqueous medium in which the platinum group metal is present in complex form and has a pH of more than 4.

It is an object of the present invention to further improve the activity and/or selectivity of the existing platinum group metal catalysts, so that the space-time yield of the reactions catalyzed by it may be increased. Furthermore, the platinum group metal should be firmly anchored to the support, so that a long on-stream time under mechanical stress can also be achieved.

We have found that this object is achieved by a supported platinum group metal catalyst obtainable by controlled electroless deposition of at least one platinum group metal from a deposition solution which comprises
  i) at least one homogeneously dissolved platinum group metal compound,
  ii) a reducing agent and
  iii) at least one control agent selected from isopolyacids and heteropolyacids of niobium, tantalum, molybdenum, tungsten and vanadium or their salts.

The invention also relates to a process for hydrogenating molecular inorganic or organic compounds, in which the compound to be hydrogenated is contacted with hydrogen in the presence of the catalyst according to the invention.

It is thought that electroless deposition of the platinum group metal onto the support in the presence of a dissolved isopolyacid and/or heteropolyacid achieves a more homogeneous coating, i.e. a more uniform distribution of the noble metal particles and a more uniform particle size on the support, which leads to an improved activity and/or selectivity. The homogeneity of the coating may be investigated, for example, with the aid of scanning electron microscopy and/or X-ray photoemission spectroscopy (ESCA).

The isopolyacid or heteropolyacid is derived from an element selected from niobium, tantalum, molybdenum, tungsten and vanadium, preferably from molybdenum, tungsten and vanadium, more preferably from tungsten. Isopolyacids are inorganic polyacids which constitute the partial anhydrides of the orthoacids of these elements and only contain central atoms of one type. Examples thereof include heptamolybdic acid, hexatungstic acid, dodecatungstic acid, bivanadic acid, decavanadic acid, hexaniobic acid and hexatantalic acid. Heteropolyacids are inorganic polyacids which, in addition to these elements, comprise a further central atom, usually arsenic, iodine, phosphorus, selenium, silicon or tellurium. Examples of such heteropolyacids include 12-molybdophosphoric acid, 12-tungstophosphoric acid, 12-tungstosilicic acid and hexatungstoiodic acid. The iso- or heteropolyacids may be formed beforehand and added to the deposition solution or formed in situ in the deposition solution from suitable precursor compounds. The degree of condensation of the iso- and/or heteropolyacids is not critical. The degree of condensation which results at the pH of the deposition solution is suitable. Useful precursor compounds are monomeric oxoacids, for example the meso- or orthoacids, or oligomeric oxoacids, for example metaacids of the elements mentioned or their salts. Useful salts of the iso- and/or heteropolyacids or their precursor compounds are in particular the alkali metal salts, especially the sodium and potassium salts, or the ammonium salts.

Examples of suitable precursor compounds include sodium tungstate, ammonium metavanadate, sodium molybdate and the like.

The molar ratio of platinum group metal to iso- and/or heteropolyacid or precursor compound therefor in the deposition solution is preferably from 0.01 to 5.0, in particular from 0.1 to 2.0, calculated as the molar ratio of platinum group metal atoms to niobium, tantalum, molybdenum, tungsten and/or vanadium atoms.

For the purposes of the invention, platinum group metals are the noble metals of the 8th transition group of the Periodic Table which do not belong to the iron group, i.e. ruthenium, rhodium, iridium, palladium, osmium and platinum. Preference is given to ruthenium, rhodium, palladium and platinum, particular preference to palladium and platinum. Combinations of the platinum group metals mentioned are also suitable, and preference is given to combinations of palladium and platinum, of palladium and rhodium, of palladium and iridium, of palladium, platinum and rhodium, and of palladium, platinum and iridium. Particular preference is given to the combination of palladium and platinum. In the combinations with palladium, palladium preferably constitutes the main component. The proportion of palladium is then preferably more than 40% by weight, preferably more than 60% by weight and more preferably more than 80% by weight, based on the total content of the platinum group metal.

The catalytically active components of the catalysts according to the invention may also comprise further elements apart from platinum group metals as promoters or dopants, which influence the activity and/or selectivity of the catalyst. These preferably include metals such as cobalt, nickel, copper, silver, gold, chromium, manganese, rhenium, aluminum, tin, lead, arsenic, antimony and bismuth, and nonmetals such as boron, carbon, silicon, nitrogen and phosphorus.

The additional components used as promoters or dopants generally amount to from 0.01 to 20% by weight, preferably from 0.1 to 15% by weight and in particular from 0.5 to 10% by weight, based on the platinum group metal content.

The platinum group metal compound is selected from palladium group metal salts and palladium group metal complexes. Preference is given to using platinum group metal complexes, in particular those in which the platinum group metal is present in the oxidation states +1 to +4. Preference is given to tetracoordinate complexes. Especially suitable are palladium(II) complexes in which palladium is present in the coordination number 4.

The platinum group metal complexes may comprise different ligands. The complexes may be prepared beforehand or in situ in the deposition solution. Suitable negatively charged ligands are, for example, selected from halides and pseudohalides such as chloride, bromide, iodide, CN, OCN and SCN, $C_1$–$C_6$-carboxylic acids such as formic acid, acetic acid and propionic acid and their salts, chelating ligands, for example ethylenediaminetetraacetic acid (EDTA), nitrilotriacetic acid, 1,2-diaminocyclohexanetetraacetic acid and their salts, aminophosphonic acids such as nitrilomethylenephosphonic acid, diketonates such as acetylacetonate, hydroxycarboxylic acids such as glycolic acid, lactic acid, tartaric acid and gluconic acid, and their salts. Examples of electronically neutral ligands include alkylnitriles such as acetonitrile, amines such as ammonia, primary, secondary and tertiary $C_1$–$C_6$-alkylamines such as ethylamine, n-propylamine, isopropylamine, n-butylamine, tert-butylamine, hexylamine, dimethylamine, diethylamine, diisopropylamine, di-n-butylamine, trimethylamine, triethylamine, tripropylamine, N,N-dimethylethylamine, N,N-dimethylisopropylamine and N,N-dimethylbutylamine, di-, tri-, tetra- and polyamines such as ethylenediamine, diethylenetriamine and triethylenetetramine, nonaromatic and aromatic cyclic amines such as pyrrolidine, piperidine, morpholine, piperazine, pyrrole and their n-$C_1$–$C_6$-alkyl derivatives, pyridine and phenanthroline, phosphines such as tertiary $C_1$–$C_6$-alkyl- and $C_6$–$C_{12}$-arylphosphines, in particular triphenylphosphine, and also sulfides such as $C_1$–$C_6$-mono- and -dialkyl sulfides, $C_6$–$C_{12}$-mono- and -diaryl sulfides and oxygen compounds, di-$C_1$–$C_6$-alkanols and phenols and also their ethers.

Particular preference is given to nitrogen-containing ligands, in particular amines, more preferably ammonia. The platinum group metal compound preferably comprises a platinum group metal complex with a nitrogen-containing ligand.

The platinum group metal content of the deposition solution is generally in the range from 0.001 to 2 g/l, preferably in the range from 0.1 to 0.5 g/l.

Preferred palladium complexes are $H_2PdHal_4$, $M_2PdHal_4$, $M_2Pd(CN)_4$, $(NH_4)_2PdHal_4$, $Pd(NH_3)_4Hal_2$, $Pd(NH_3)_4(NO_3)_2$ and $Pd(NH_3)_4(CN)_2$, where M is an alkali metal, in particular sodium or potassium, and Hal is a halogen atom, in particular chlorine, bromine or iodine.

Preferred further platinum group metal complexes are $(NH_4)_2IrCl_6$, $H_2PtCl_4$, $(NH_4)_2PtCl_4$, $Na_2PtCl_4$ and $K_2PtCl_4$.

The deposition solution further comprises at least one reducing agent in dissolved form. Useful reducing agents are any substances or substance mixtures whose redox potential is below the redox potential of the platinum group metal compound used. Preference is given to substances having a standard potential in an aqueous medium of less than +0.5 volt, preferably having a standard potential of less than 0 volt.

Examples of suitable reducing agents include formic acid or α-hydroxycarboxylic acids such as citric acid, lactic acid, tartaric acid and in particular the salts of the carboxylic acids, preferably the alkali metal, alkaline earth metal, ammonium and $C_1$–$C_{10}$-alkylammonium salts, phosphorous or hypophosphorous acid, the salts of phosphorous or hypophosphorous acid, in particular the alkali metal or alkaline earth metal salts, $C_1$–$C_{10}$-alkanols such as methanol, ethanol and isopropanol, sugars such as aldoses and ketoses in the form of mono-, di- and oligosaccharides, in particular glucose, fructose and lactose, aldehydes such as formaldehyde, boron-hydrogen compounds, for example borohydrides, boranes, metal borates and borane complexes, for example diborane, sodium borohydride and aminoboranes, in particular trimethylaminoborane, hydrazine and alkylhydrazines such as methylhydrazine, hydrogendithionites and dithionites, in particular sodium and potassium hydrogendithionite, sodium, potassium and zinc dithionite, hydrogensulfites and sulfites, in particular sodium and potassium hydrogensulfite, sodium, potassium and calcium sulfite, hydroxylamine and urea, and also mixtures thereof.

Preferred reducing agents are sodium and potassium hypophosphite, ammonium formate, trimethylamineborane, sodium borohydride, sodium dithionite and sodium hydrogendithionite, and also mixtures of ammonium formate and sodium hypophosphite.

In general, at least one redox equivalent, based on the sum of the platinum group metals and added components (for example promoters/dopant components) of reducing agents is used. Preference is given to using the reducing agent in excess. Especially suitable is a molar ratio of reducing agent to platinum group metal of from 10:1 to 100:1 and more preferably from 20:1 to 60:1, for example about 30:1, about 40:1 or about 50:1.

The deposition solution preferably has a pH of more than 6. This is preferably in the range from 7 to 14, in particular from 8 to 12. To this end, it may be necessary to add a base to the deposition solution, in order to attain the desired pH. Bases are any substances or compounds which are suitable for adjusting the pH of the aqueous medium to the desired value. In particular, the bases used are those which have complex-stabilizing properties, i.e. have at least partial Lewis base character. Preference is given to selecting the base among metal oxides, metal hydroxides, in particular alkali metal hydroxides such as sodium hydroxide and potassium hydroxide, metal carbonates, in particular alkali metal and alkaline earth metal carbonates such as lithium carbonate, sodium carbonate, potassium carbonate, magnesium carbonate and calcium carbonate, nitrogen bases, in particular ammonia, primary, secondary and tertiary amines, such as those described previously among the nitrogen-containing complex ligands. Likewise suitable are buffer systems, in particular those of the abovementioned bases, the salts of the abovementioned bases and/or suitable acids. Particularly preferred bases are ammonia and sodium hydroxide solution.

The deposition solution is generally aqueous, i.e. it contains at least 10% by weight, preferably at least 30% by weight and in particular at least 50% by weight of water. The portion other than water is preferably selected from water-miscible solvents such as methanol, ethanol, n-propanol, isopropanol, n-butanol, sec-butanol, tert-butanol, tetrahydrofuran or dioxane.

The supports used may be any catalyst support known to those skilled in the art, either metallic or nonmetallic. Suitable metallic supports are described, for example, in WO 00/59635, whose disclosure content is referred to. Nonmetallic supports are generally selected from mineral materials or plastics.

In the present context, the term "mineral materials" quite generally encompasses nonmetallic inorganic materials such as natural and synthetic minerals, glasses, ceramics, etc. The mineral material used is preferably a glass. Preference is given to glasses composed of molten silicon dioxide or molten quartz, and also glasses based on alkali metal silicate, alkaline earth metal silicate, borosilicate, aluminosilicate and lead silicate. Further preferred support materials are borate, phosphate, germanate, chalcogenide and halide glasses, for example composed of beryllium fluoride.

Preference is also given to the mineral material used as a support being selected from ceramic materials. Useful ceramic materials may be prepared from metal oxides, borides, nitrides and/or carbides. The ceramic materials used according to the invention may be glazed or unglazed, crystalline or semicrystalline. For the process according to the invention, preference is given to using ceramics made of base materials which are selected from aluminum oxide, silicon carbide, silicon nitride, zirconium dioxide and mixtures thereof. Preference is further given to using ceramics which contain cations, as is the case, for example, in chelatite, steatite, cordierite, anorthite, mullite or pollucite. Preference is further given to ceramic composite materials.

Nonmetallic supports generally have to be activated. "Activation" of the support refers to a procedure in which seeds are formed on the surface of the support which support the subsequent electroless deposition of the platinum group metal. The seeds generally consist of a metal, preferably a platinum group metal, in particular palladium. To activate it, the support is preferably treated with the solution of a sensitizer and then with the solution of a platinum group metal salt. Useful sensitizers are generally reducing agents, and particular preference is given to tin(II) compounds, in particular tin(II) chloride, and titanium(III) compounds, optionally in combination with other reducing agents. Other reducing agents advantageous as sensitizers include salts of hypophosphorous acid. The activation is described, for example, in EP-A-0 875 235, and reference is made to its disclosure content.

The deposition is generally effected at a temperature in the range from 0 to 100° C., preferably in the range from 30 to 100° C. and in particular in the range from 40 to 85° C.

To deposit the platinum group metal, the support is, for example, contacted with the fully formulated deposition solution. Alternatively, the support may initially be contacted with a solution of the reducing agent and the control agent which optionally contains all or some of the optional constituents of the deposition solution. The platinum group metal and the remaining optional constituents are then added at the deposition temperature or a temperature, for example, up to 30° C. lower. A further alternative is to contact the support with a solution of the platinum group metal compound and the control agent and then to add a solution of the reducing agent.

In the process according to the invention, it has proven advantageous to ensure sufficient circulation of the deposition solution during the deposition of the platinum group metal on the support by, for example, pumping or stirring.

The deposition solution is left in contact with the support sufficiently long to achieve electroless deposition of the platinum group metal on the support. The necessary reaction time is generally between 0.5 and 500 minutes, preferably 1 and 300 minutes and more preferably between 2 and 60 minutes. In general, more than 70% by weight, preferably more than 80% by weight and more preferably more than 90% by weight of the platinum group metals used is deposited on the support. The platinum group metal is generally so firmly bound to the support that it is not significantly removed by contact with liquids and gases when used in catalytic reactions. The elements on which the control agent is based are found on the catalyst only in negligible amounts.

The catalysts according to the invention are suitable for the hydrogenation of organic and inorganic compounds, and in particular for organic compounds such as olefins, e.g. ethylene, propylene, acetylene and butadiene, carbonyl compounds, e.g. aldehydes and ketones, aromatics, e.g. benzene, and more preferably for hydrogenating oxygen for preparing hydrogen peroxide.

The present invention further provides a process for preparing hydrogen peroxide by contacting the oxygen and the hydrogen in a liquid medium, preferably a substantially aqueous solution, with a catalyst according to the invention.

Suitable catalysts for the synthesis of $H_2O_2$ are described, for example, in EP-A-068 862, EP-A-201 614 and EP-A-448 884. Particular preference is given to tubular reactors in which the catalyst according to the invention is present as a bed or in the form of cylindrically constructed catalyst units. Appropriate shaping for the support, as previously described, may ensure optimum flow conditions for gas and liquid.

The liquid phase preferably trickles from top to bottom over the catalyst bed. The gas may be conducted in cocurrent or in countercurrent, preferably in cocurrent.

Preference is given to feeding the hydrogen to the reactor via one or more intermediate feeds downstream of the metering point of the oxygen or the air. The superficial velocity of reaction gas and reaction medium is preferably in the range from about 20 to 7000 m/h, more preferably in the range from 50 to 1400 m/h.

The reaction medium is preferably water and/or $C_1$–$C_3$-alkanols, in particular water and/or methanol. When the reaction medium used is water, up to 20% by weight of the alcohol, preferably methanol, may be added. When an alcoholic reaction medium is used, it may comprise 40% by weight, preferably up to 20% by weight and more preferably up to 5% by weight, of water. Very particular preference is given to using water as the sole reaction medium. To stabilize the hydrogen peroxide against decomposition, acids whose pKa is preferably less than that of acetic acid, in particular mineral acids such as sulfuric acid, phosphoric acid or hydrochloric acid, are added to the reaction medium. The acid concentration is generally at least $10^{-4}$ mol/liter, preferably from $10^{-3}$ to $10^{-1}$ mol/liter. Traces of bromide or chloride in concentrations of from 1 to 1000 ppm, preferably from 5 to 700 ppm and more preferably from 50 to 600 ppm are generally also added. It is also possible, however, to use other stabilizers, for example formaldehyde.

The reaction gas which, in addition to hydrogen and oxygen, may also comprise other inert gases such as nitrogen or noble gases generally has $O_2$:$H_2$ ratios in the range from 2:1 to 1000:1. Preference is given to using molar ratios in the range from 5:1 to 100:1, in particular 20:1 to 100:1. The oxygen used in the reaction gas may also be added to the reaction gas in the form of air.

In a preferred embodiment, the reaction gas is circulated. In this case, the molar ratio in the fresh gas mixture is in the region of stoichiometry, preferably in the range from 1.5:1 to 0.5:1. The $O_2$:$H_2$ molar ratio in the cycle gas should be in the range from 5:1 to 1000:1, preferably in the range from 20:1 to 100:1. The reaction may be carried out at atmospheric pressure or else at elevated pressures of up 200 bar.

The pressure is preferably from 10 to 100 bar, in particular from 10 to 80 bar. The reaction temperature may be in the range from 0 to 80° C., and preference is given to working in the range from 5 to 60° C. and in particular from 25 to 55° C. Preference is given to selecting the partial pressures of the reaction gases in the reaction gas mixture in the reactor and also in the cycle gas in such a way that the hydrogen concentration under the reaction conditions is below the lower explosion limit.

The process described allows hydrogen peroxide solutions having hydrogen contents of up to 2% by weight, preferably in the range from 3 to 25% by weight, to be prepared. The concentration may be preselected in the desired manner by adjusting the streams. Long-term investigations have shown that even after more than 40 days of operating time, very little reduction, if any, in the catalyst activity and selectivity is to be noted.

In contrast to the catalysts known from the prior art, the catalysts prepared according to the invention have excellent catalyst properties. They are highly active and very selective in hydrogenation reactions. The process also achieves particularly good adhesion of the platinum group metal particles to the support, which is why the catalysts prepared according to the invention achieve particularly long on-stream times.

The invention is illustrated in detail with the aid of the appended figure and the examples which follow.

FIG. 1 shows the variation with time of the space-time yields for the direct hydrogen peroxide synthesis catalyzed by a catalyst according to the invention or a comparative catalyst.

PREPARATION OF THE CATALYSTS

EXAMPLE 1 (=COMPARATIVE EXAMPLE, CAT. B1)

1200 g of steatite support from Ceramtec in the form of spheres of 2 mm diameter were washed in succession with aqueous sodium hydroxide solution, 25% sulfuric acid and distilled water. The spheres pretreated in this way were then activated on a suction filter by allowing a solution A (=5 g/l of $SnCl_2$+10 ml/l of conc. hydrochloric acid) to act for 3 min, then, after filtering off and washing with 0.5 l of distilled water, allowing a solution B (=0.2 g/l of $PdCl_2$+1 ml/l of conc. hydrochloric acid) to act for 3 min. After renewed filtration and washing with water, the entire procedure was repeated and finally, the spheres were washed three times with 0.5 l of distilled water each time.

The spheres were installed damp in a glass tube and admixed with a solution C (=70 g/l of $NH_4Cl$, 23 g/l of $NH_3$ and 30 g/l of sodium hypophosphite). This solution was pumped through the tube with the aid of a pump in such a way that the spheres only just moved and formed a fluidized bed. A reservoir which, at the same time, served as a gas separator was used to recycle the solution back to the entrance of the glass tube. The glass tube was also provided with a jacket which is filled with heating liquid. The temperature in the solution was brought to 40+/−0.5° C. with circulation by pumping before the coating. 20 g of a solution D of 2.8 mg of hexachloroplatinic acid and 526 mg of sodium tetrachloropalladate in water were then added and the reaction initiated. After 1 hour, the reaction was complete. The solution was drained off and flushing was effected using water. The catalyst prepared in this way had a Pd content of 145 mg/kg, corresponding to a degree of deposition of 92%.

EXAMPLE 2 (=CAT. B2)

The catalyst preparation of Example 1 was repeated, with the difference that solution D additionally contains 405 mg of sodium tungstate.

The properties of the catalysts were tested in the direct synthesis of hydrogen peroxide from hydrogen and oxygen.

EXAMPLE 3

A jacketed reactor having an internal diameter of 2.1 cm and a length of 2.00 m was charged with the catalyst B1. At 40° C. and 50 bar of pressure, a solution of 5 g/l of phosphoric acid and 120 mg/l of hydrogen bromide in water was allowed to trickle at a rate of 1.0 kg/h over the catalyst bed. At the same time, a mixture of 3% of hydrogen and 97% of oxygen was pumped with the aid of a gas compressor at a rate of 10 400 l (STP)/hour from top to bottom in a cycle over the catalyst bed. The gas mixture is generated with the aid of two mass flow meters for hydrogen and oxygen. Its composition is determined and controlled with the aid of a thermal conductivity detector, over which a small bleed stream is passed as an offgas stream.

The amount of hydrogen consumed by the reaction to give hydrogen peroxide and water was calculated from the mass streams of the gases introduced and the offgas stream.

The product mixture leaving the reaction tube was separated from the gases in a separator while still under pressure and conveyed out of the plant in liquid form. A mass balance was conducted of the mass stream against the feed stream. The hydrogen peroxide content in the liquid effluents was determined by titration.

The mass of the effluent stream, the content of hydrogen peroxide and the amount of hydrogen consumed were used to calculate the selectivity based on hydrogen. The space-time conversion (STC) is determined as the consumption of hydrogen in moles per unit time based on the volume of the catalyst bed.

The space-time yield (STY) is determined from the amount of hydrogen peroxide formed per unit time based on the volume of 690 ml of catalyst bed in the tubular reactor. The results are summarized in the Table 1 which follows. The variation of the space-time yield with time is shown by FIG. 1.

EXAMPLE 4

Example 3 was repeated, with the different that catalyst B2 was used. This measure leads to a higher space-time yield owing to higher activity and a somewhat better selectivity (cf. Table 1 and FIG. 1). It can be seen that the STY for the catalyst according to the invention is always above the STY of the comparative catalyst.

| No. | Catalyst | T [° C.] | Selectivity | STC [$molH_2$/lh] | STY [$gH_2O_2$/lh] | Running time |
|---|---|---|---|---|---|---|
| 3 | B1 | 50° C. | 79% | 3.0–2.7 | 85–77 | 90 h |
| 4 | B2 | 50° C. | 81% | 3.4–3.0 | 100–85 | >400 h |

We claim:

1. A supported platinum group metal catalyst obtained by controlled electroless deposition of at least one platinum group metal from a deposition solution which comprises
   i) at least one homogeneously dissolved platinum group metal compound,
   ii) a reducing agents, and
   iii) at least one control agent selected from the group consisting of an isopolyacid of niobium, an isopolyacid of tantalum, an isopolyacid of molybdenum, an isopolyacid of tungsten, an isopolyacid of vanadium, a salt of an isopolyacid of niobium, a salt of an isopolyacid of tantalum, a salt of an isopolyacid of molybdenum, a salt of an isopolyacid of tungsten, a salt of an isopolyacid of vanadium, a heteropolyacid of niobium, a heteropolyacid of tantalum, a heteropolyacid of molybdenum, a heteropolyacid of tungsten, a heteropolyacid of vanadium, a salt of a heteropolyacid of niobium, a salt of a heteropolyacid of tantalum, a salt of a heteropolyacid of molybdenum, a salt of a heteropolyacid of tungsten, a salt of a heteropolyacid of vanadium and mixtures thereof, thereby obtaining said supported platinum group metal catalyst, wherein the elements on which said control agent is based are detected in the catalyst only in negligible amounts.

2. The catalyst as claimed in claim 1, wherein the platinum group metal is palladium or a mixture of palladium and platinum.

3. The catalyst as claimed in claim 1, wherein the platinum group metal compound comprises a platinum group metal complex having a nitrogen-containing ligand.

4. The catalyst as claimed in claim 1, wherein the deposition solution has a pH of from 8 to 12.

5. The catalyst as claimed in claim 1, wherein the isopolyacid or heteropolyacid is formed in situ in the deposition solution from a monomeric or oligomeric oxoacid.

6. The catalyst as claimed in claim 1, wherein the support has been activated before the deposition.

7. The catalyst as claimed in claim 6, wherein the support has been treated to activate it with a solution of a sensitizer and then with the solution of a platinum group metal salt.

8. The catalyst as claimed in claim 1, wherein the support is at least one member selected from the group consisting of ceramic materials, glasses and mixtures thereof.

9. A process for hydrogenating molecular inorganic or organic compounds, comprising:

contacting a compound to be hydrogenated with hydrogen in the presence of a catalyst as claimed in claim 1.

10. The process as claimed in claim 9, comprising hydrogenating molecular oxygen to obtain hydrogen peroxide.

11. The process as claimed in claim 10, wherein the oxygen and the hydrogen are contacted with the catalyst in a liquid medium.

12. A process for preparing a catalyst as claimed in claim 1, comprising:

depositing at least one platinum group metal onto a support by electroless deposition from a deposition solution which comprises i) at least one homogeneously dissolved platinum group metal compound, ii) a reducing agent, and iii) at least one control agent selected from the group consisting of an isopolyacid of niobium, an isopolyacid of tantalum, an isopolyacid of molybdenum, an isopolyacid of tungsten, an isopolyacid of vanadium, a salt of an isopolyacid of niobium, a salt of an isopolyacid of tantalum, a salt of an isopolyacid of molybdenum, a salt of an isopolyacid of tungsten, a salt of an isopolyacid of vanadium, a heteropolyacid of niobium, a heteropolyacid of tantalum, a heteropolyacid of molybdenum, a heteropolyacid of tungsten, a heteropolyacid of vanadium, a salt of a heteropolyacid of niobium, a salt of a heteropolyacid of tantalum, a salt of a heteropolyacid of molybdenum, a salt of a heteropolyacid of tungsten, a salt of a heteropolyacid of vanadium and mixtures thereof.

13. The catalyst as claimed in claim 1, wherein said platinum group metal is uniformly distributed on the support.

14. The catalyst as claimed in claim 1, wherein said platinum group metal has a uniform particle size.

15. The catalyst as claimed in claim 1, wherein said isopolyacid is heptamolybdic acid, hexatungstic acid, dodecatungstic acid, bivanadic acid, decavanadic acid, hexaniobic acid or hexatantalic acid.

16. The catalyst as claimed in claim 1, wherein said heteropolyacid is 12-molybdophosphoric acid, 12-tungstophosphoric acid, 12-tungstosilicic acid or hexatungstoiodic acid.

17. The catalyst as claimed in claim 1, wherein said heteropolyacid further comprises at least one element selected from the group consisting of arsenic, iodine, phosphorous, selenium, silicon, tellurium and mixtures thereof.

18. The catalyst as claimed in claim 1, wherein a molar ratio of 1) said platinum group metal to 2) said isopolyacid, said heteropolyacid or a mixture thereof, in the deposition solution is from 0.01 to 5.0, calculated as the molar ratio of platinum group metal atoms to at least one member selected from the group consisting of niobium, tantalum, molybdenum, tungsten, vanadium and mixtures thereof.

19. The catalyst as claimed in claim 1, wherein said platinum metal compound is a palladium group metal salt or a palladium group metal complex.

20. The catalyst as claimed in claim 1, comprising a palladium (II) complex in which the palladium is present in the coordination number 4.

21. The catalyst as claimed in claim 1, wherein a content of said platinum group metal in the deposition solution is 0.001 to 2 g/l.

* * * * *